(12) United States Patent
Yogeeswari

(10) Patent No.: US 10,954,197 B2
(45) Date of Patent: Mar. 23, 2021

(54) CATHEPSIN-D AND ANGIOGENESIS INHIBITORS AND COMPOSITIONS THEREOF FOR TREATING BREAST CANCER

(71) Applicant: YOGEE'S BIOINNOVATIONS PRIVATE LIMITED, Hyderabad (IN)

(72) Inventor: Perumal Yogeeswari, Hyderabad (IN)

(73) Assignee: YOGEE'S BIOINNOVATIONS PRIVATE LIMITED, Hyderabad (IN)

(*) Notice: Subject to any disclaimer, the term of this patent is extended or adjusted under 35 U.S.C. 154(b) by 0 days.

(21) Appl. No.: 16/492,434

(22) PCT Filed: Mar. 5, 2018

(86) PCT No.: PCT/IN2018/050120
§ 371 (c)(1),
(2) Date: Sep. 9, 2019

(87) PCT Pub. No.: WO2018/163204
PCT Pub. Date: Sep. 13, 2018

(65) Prior Publication Data
US 2020/0039944 A1 Feb. 6, 2020

(30) Foreign Application Priority Data
Mar. 8, 2017 (IN) .............................. 201741004642

(51) Int. Cl.
C07D 249/12 (2006.01)
A61K 31/4196 (2006.01)
A61P 35/00 (2006.01)
C07D 417/12 (2006.01)

(52) U.S. Cl.
CPC ............ C07D 249/12 (2013.01); A61P 35/00 (2018.01); C07D 417/12 (2013.01)

(58) Field of Classification Search
CPC .......................... C07D 249/12; A61K 31/4196
See application file for complete search history.

(56) References Cited

U.S. PATENT DOCUMENTS

| 6,605,589 | B1 | 8/2003 | Uckun et al. |
| 9,827,337 | B2 | 11/2017 | Vasiljeva et al. |
| 2006/0166966 | A1 | 7/2006 | Black |
| 2009/0099157 | A1 | 4/2009 | Ameriks et al. |
| 2009/0264412 | A1 | 10/2009 | Kampen et al. |
| 2017/0320854 | A1* | 11/2017 | Collin ................ A61K 31/4439 |

FOREIGN PATENT DOCUMENTS

| WO | 2004033445 A1 | 4/2004 |
| WO | WO2004033445 A1 | 4/2004 |
| WO | 2008100621 A2 | 8/2008 |
| WO | WO2008100621 A2 | 8/2008 |

OTHER PUBLICATIONS

Yamazaki, Bioorganic & Medicinal Chemistry Letters, 2006, vol. 16, No. 5, p. 1371-1379 (Year: 2006).*
International Search Report dated Jul. 5, 2018 for PCT/IN2018/050120.
Written Opinion dated Jul. 5, 2018 for PCT/IN2018/050120.

* cited by examiner

*Primary Examiner* — Karen Cheng
(74) *Attorney, Agent, or Firm* — Schmeiser, Olsen & Watts, LLP

(57) ABSTRACT

Cathepsin-D and angiogenesis inhibitors and compositions thereof for treating breast cancer are provided. More particularly, the embodiments relate to the design and synthesis of inhibitors of Cathepsin D, which exhibits antiproliferative activity and also inhibits angiogenesis. Also provided are compositions thereof for treating breast cancer.

7 Claims, No Drawings

CATHEPSIN-D AND ANGIOGENESIS INHIBITORS AND COMPOSITIONS THEREOF FOR TREATING BREAST CANCER

CROSS-REFERENCE TO RELATED APPLICATIONS

This application claims priority to PCT Application No. PCT/IN2018/050120, having a filing date of Mar. 5, 2018, based on IN 201741004642, having a filing date of Mar. 8, 2017, the entire both contents of which are hereby incorporated by reference.

FIELD OF TECHNOLOGY

The following relates to Cathepsin-D and angiogenesis inhibitors and compositions thereof for treating breast cancer. More particularly, the following relates to design and synthesis of inhibitors of Cathepsin D which exhibits antiproliferative activity and also inhibits angiogenesis. The following also relates to compositions thereof for treating breast cancer.

BACKGROUND

Cathepsin has been widely implicated as playing a causal role in cancer by facilitating tumor progression. In order for a tumor to become malignant, cells must invade beyond the tissue it originated and enter circulation. The estrogen-dependent neoplasm leads to activation of P53 pathway which in turn releases lysosomal aspartic protease Cathepsin D into the cytoplasm. Conclusively, release of tumor growth factors due to extracellular matrix degradation by Cathepsin D. This further leads to tumor growth, angiogenesis and metastasis. Besides, Cathepsin D is also implicated to be dispensable for MHC class II antigen presentation and also known to display in-vitro specificity as beta secretase in neurological disorders like Alzheimer's disease.

Many studies have shown a clear link between cathepsin expression and tumor invasion. Cathepsin expression is an accurate biomarker of more advanced endometrial cancer, glioblastoma cell lines, breast cancer, and can be used to predict aggressiveness of the tumor.

Cathepsin D, an aspartate protease, has been studied extensively both clinically and in cell culture, and is overproduced in and over secreted from tumor cells. Cathepsin D in breast cancer is overexpressed by 2 to 50-fold compared to its concentration in other cells, such as fibroblasts or normal mammary glands. Overexpressed Cathepsin D areas are located in breast cancer tissue and not in tumor fibroblasts. Cathepsin D is an intracellular aspartic peptidase found mainly in lysosomes. It has a number of housekeeping functions, including the degradation of cellular and phagocytosed proteins. Increased Cathepsin D activity in the cytosol of malignant breast carcinomas suggests that it may play an active role in metastatic spread. Cathepsin D level in primary breast cancer cytosol is an independent prognostic parameter associated with occurrence of clinical metastases and shorter survival.

Cathepsin D has been studied over the last three decades, mainly from the perspective of its role in cancer development, and several peptide and non-peptide Cathepsin-D inhibitors were synthesized. Diazoketone compounds such as diazoacetyl-DL-norleucine methyl ester (DAN) and 1,2-epoxy-3-(p-nitrophenoxy)propane (EPNP) were synthesized and shown inhibitory effect on Cathepsin D. Hydroxyethyl amine isosteres have also been utilized in the design of cathepsin D inhibitors for a structure based combinatorial library. N-piperazine (S)-hydroxyethyl amine with a 2-carboxylic amide in the axial position found effective against Cathepsin D.

Another approach adopted in which peptide derivatives is modeled on the basis of pepstatin which inhibit renin and acid protease. Also, Cathepsin D inhibitors were developed wherein the scissile dipeptide unit in a substrate sequence was replaced with a statine (Sta) residue or by a phenylstatine (Pst) unit.

The synthesis and structure activity relationships of novel small molecule Cathepsin D Inhibitors has been disclosed in Bioorganic Medicinal Chemistry Letters 1999, 9(17), 2531-6. The International Patent Publication No. WO 2004/033445 describes compounds which are useful for treating diseases in which Cathepsin-dependent bone resorption was indicated. The U.S. Pat. No. 6,605,589 describes a method of inducing apoptosis in a cancer cell comprising contacting the cell with an apoptosis inducing amount of a cathepsin inhibitor, wherein the Cathepsin inhibitor is CATI-1 (Z-Phe-Gly-NHO-Bz; where Z is benzyloxycarbonyl, —NHO— is hydroxylamine linkage, and Bz is benzoyl). The U.S. Pat. No. 9,827,337 relates to Cathepsin-binding compounds bound to a carrier comprising a diagnostic moiety, for use in the diagnosis of inflammatory diseases, and/or for use in the diagnosis of neoplastic diseases, wherein the Cathepsin-binding compound binds to inflammatory cells of the tumour stroma.

There is still little known about substrate specificity and specific inhibitors for Cathepsin D. Accordingly, there is a need for the synthesis of compounds which are specific for the inhibition of the activity of Cathepsin D and which may be used in the treatment of breast cancer like metastatic disease.

Angiogenesis is the formation of new blood vessels during cancer progression to enable migration, growth and differentiation of cells. Cancer cells release chemical signals to initiate angiogenesis and inhibiting them is a crucial step in preventing cancer growth and metastasis which is spread of cancer to other parts of the body. Angiogenesis inhibitors interfere with these chemical signals and prevent cancer growth and metastasis. Currently angiogenesis inhibitors like Bevacizumab, Everolimus, etc have been used in combination with other anticancer drugs; and there are no drugs which exhibit both anticancer and antiangiogenic activities.

Surprisingly, inventors of embodiments of the present invention have developed novel anticancer compounds which also exhibit antiangiogenic activity.

SUMMARY

An aspect relates to developing a therapeutically active chemical compound that has specificity to Cathepsin D and acts both as anticancer agent and antiangiogenic agent.

In an aspect of embodiments of the present invention is to develop compositions of therapeutically active chemical compound to treat breast cancer including triple positive and triple negative type.

In an aspect of embodiments of the present invention is to establish bioactivity of therapeutically active chemical compound effective in treating breast cancer with no acute toxicity.

Accordingly, there are provided inhibitors of Cathepsin D which exhibit antiproliferative activity and also inhibit angiogenesis. In general, there are provided Cathepsin D inhibiting compounds and compositions thereof for the treatment of breast cancer.

In an aspect of embodiments of the invention, there is provided a compound of Formula (I)

Formula (I)

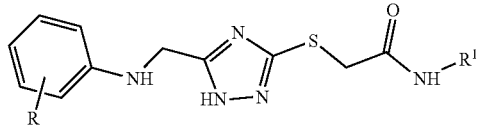

or a pharmaceutically acceptable salt thereof;
wherein
a) R is hydrogen or $C_1$-$C_6$ alkyl, and
b) $R^1$ is aryl or heteroaryl optionally substituted with one or more substituent.

In embodiments of the invention, there is provided a compound of Formula (I), wherein R is hydrogen or $CH_3$.

In embodiments of the invention, there is provided a compound of Formula (I), wherein $R^1$ is phenyl or benzthiazolyl optionally substituted with one or more substituent selected from $CH_3$, $OCH_3$, Cl, F, Br, OH, $CONH_2$, $NH_2$, $HNCOCH_3$, $NO_2$, $COCH_3$, COOH, $CF_3$, CN and the like.

In an aspect of embodiments of the invention, there is provided a compound of Formula (II)

Formula (II)

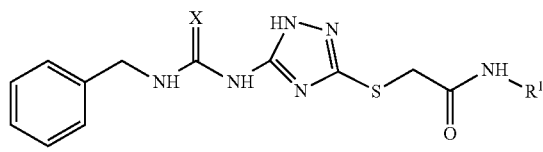

or a pharmaceutically acceptable salt thereof;
wherein
a) X is O or S, and
b) $R^1$ is aryl or heteroaryl optionally substituted with one or more substituent.

In embodiments of the invention, there is provided a compound of Formula (II), wherein $R^1$ is phenyl optionally substituted with one or substituent selected from $CH_3$, $OCH_3$, Cl, F, Br, OH, $CONH_2$, $NH_2$, $HNCOCH_3$, $NO_2$, $COCH_3$, COOH, $CF_3$ or CN.

In embodiments of the invention, there is provided a compound of Formula (II), wherein $R^1$ is benzthiazolyl optionally substituted with one or substituent selected from $CH_3$, $OCH_3$, Cl, F, Br, OH, $CONH_2$, $NH_2$, $HNCOCH_3$, $NO_2$, $COCH_3$, COOH, $CF_3$ or CN.

In embodiments of the invention, there is provided a compound of Formula (I) selected from the group comprising of:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;
N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-((5-((m-tolylamino)methyl)-1H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide or
a pharmaceutically acceptable salt thereof.

In embodiments of the invention, there is provided a compound of Formula (II) selected from the group comprising of:
2-((5-(3-benzylthioureido)-1H-1,2,4-triazol-3-yl)thio)-N-(5-nitrobenzo[d]thiazol-2-yl)acetamide;
N-(3-acetylphenyl)-2-((5-(3-benzylthioureido)-1H-1,2,4-triazol-3-yl)thio)acetamide;
2-((5-(3-benzylureido)-1H-1,2,4-triazol-3-yl)thio)-N-(4-nitrophenyl)acetamide;
N-(3-acetylphenyl)-2-((5-(3-benzylureido)-1H-1,2,4-triazol-3-yl)thio)acetamide;
2-((5-(3-benzylureido)-1H-1,2,4-triazol-3-yl)thio)-N-(2-methyl-4-nitrophenyl)acetamide
or a pharmaceutically acceptable salt thereof.

In an aspect of embodiments of the invention, there is provided a pharmaceutical composition for treatment of breast cancer, the composition comprising a compound of Formula (I) or a compound of Formula (II) or a pharmaceutically acceptable salt thereof. In embodiments of the invention, the pharmaceutical composition further comprises one or more pharmaceutically acceptable excipients.

In embodiments, the composition comprises a transdermal delivery system. In some embodiments, the composition is a transdermal patch.

In an aspect of embodiments of the invention, there is provided a process for the preparation of a compound of Formula (I), Formula (I)

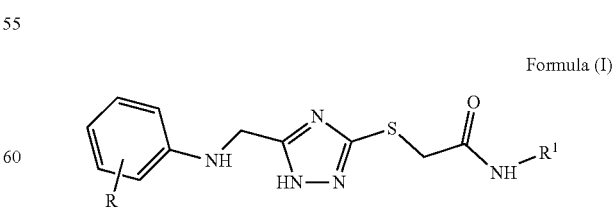

wherein
a) R is hydrogen or $C_1$-$C_6$alkyl, and
b) $R^1$ is aryl or heteroaryl optionally substituted with one or more substituent;

the process comprising steps of:

a) reacting a compound of Formula (A) with ethyl bromoacetate in presence of suitable base and solvent to obtain a compound of Formula (B);

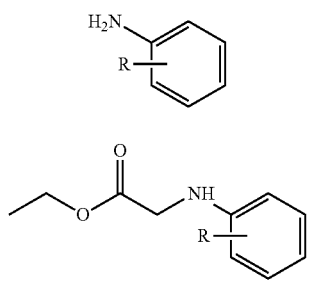

b) treating the compound of Formula (B) with hydrazine hydrate to obtain a compound of Formula (C);

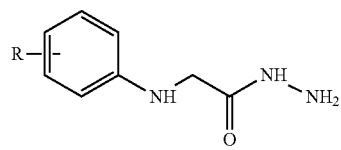

c) treating the compound of Formula (C) with ammonium formate and thiourea to obtain a compound of Formula (D); and

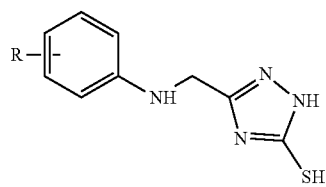

d) reacting the compound of Formula (D) with substituted α-chloroacetanilide of Formula (H) in the presence of a suitable base to obtain the compound of Formula (I)

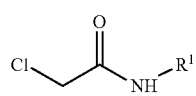

In an aspect of embodiments of the invention, there is provided a process for the preparation of a compound of Formula (II),

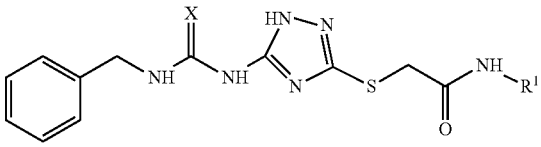

Wherein,
a) X is O or S, and
b) $R^1$ is aryl or heteroaryl optionally substituted with one or more substituent;

the process comprising steps of:

a) reacting a compound of Formula (E) with 3-Amino-1H-1,2,4-triazole-5-thiol of Formula (F) to obtain a compound of Formula (G); and

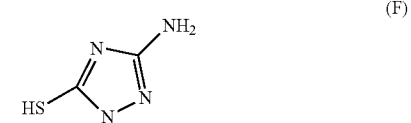

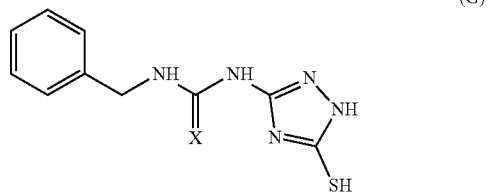

b) reacting the compound of Formula (G) with substituted α-chloroacetanilide of Formula (H) to obtain a compound of Formula (II).

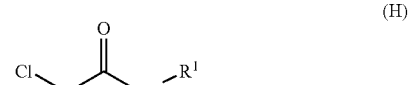

DETAILED DESCRIPTION

The inventors of embodiments of the present invention have surprisingly developed novel compounds which act as inhibitors of Cathepsin D and exhibit both as anticancer and antiangiogenic activities.

The term 'C1-C6 alkyl' as used herein refers to straight or branched chain hydrocarbon groups of 1 to 6 carbon atoms. Typical, non-limiting examples of C1-C6 alkyl include methyl, ethyl, propyl, isopropyl, butyl, sec-butyl, tert-butyl, pentyl, hexyl and the like. Further, C1-C6 alkyl may optionally be substituted with one or more substituents. Typical, non-limiting examples of substitutents include hydroxyl, halo, alkyl, amino, alkylamino, arylamino, alkoxy, aryloxy, amido, alkanoyl, nitro, cyano, sulfonic acid, sulfate, carboxylic acid, phosphate and the like.

The term 'aryl' as used herein refers to monocyclic, bicyclic or tricyclic aromatic groups containing from 6 to 14 carbons in the ring. Typical, non-limiting examples of aryl group include phenyl, naphthyl, phenanthrenyl, anthracenyl, indenyl, azulenyl, biphenyl, biphenylenyl and fluorenyl groups. Further, aryl group may be optionally substituted with one or more substituents. Typical, non-limiting examples of substitutents include hydroxyl, halo, alkyl, amino, alkylamino, arylamino, alkoxy, aryloxy, amido, alkanoyl, nitro, cyano, sulfonic acid, sulfate, carboxylic acid, phosphate and the like.

The term 'heteroaryl' as used herein refers to a 5 to 14 membered monocyclic, bicyclic or tricyclic aromatic ring containing 1-4 heteroatoms selected from O, S, and N. Typical, non-limiting examples of heteroaryl include pyridine, pyrimidine, pyridazine, furan, pyrrol, thiophene, thiazole, oxazole, isooxazole, benzofuran, benzothiophene, indole, pyranopyrrole, benzopyran, benzocyclohexyl, naphthyridine, acridine, arsindole, carbazole, chromane, chromene, cinnoline, imidazole, indazole, indoline, indolizine, isobenzofuran, isochromene, isoindole, isoindoline, isoquinoline, isothiazole, oxadiazole, perimidine, phenanthridine, phenanthroline, phenazine, phthalazine, pteridine, purine, pyran, pyrazine, pyrazole, pyrrolizine, quinazoline, quinoline, quinolizine, quinoxaline, tetrazole, thiadiazole, triazole, xanthene, and the like. Further, aryl group may be optionally substituted with one or more substituents. Typical, non-limiting examples of substitutents include hydroxyl, halo, alkyl, amino, alkylamino, arylamino, alkoxy, aryloxy, amido, alkanoyl, nitro, cyano, sulfonic acid, sulfate, carboxylic acid, phosphate and the like.

The term 'pharmaceutically acceptable salts' as used herein refers to salts of the compounds of embodiments of the invention wherein the parent compound is modified by making a salt with an acid or base. When a compound of embodiments of the invention contains a relatively acidic functional group, a base addition salt can be obtained by treating with desired base. Examples of the base addition salts include salts of sodium, potassium, calcium, ammonium, organic amine, or magnesium, or similar salts. When a compound of embodiments of the invention contains a relatively basic functional group, an acid addition salt can be obtained by treating with desired acid. Examples of the acid addition salts include salts of inorganic acids including hydrochloric, hydrobromic, nitric, carbonic, hydrocarbonic, phosphoric, hydrophosphoric, dihydrophosphoric, sulfuric, hydrosulfuric, hydriodic, or phosphorous acids and the like; as well as salts of organic acids including acetic, propionic, isobutyric, maleic, malonic, benzoic, succinic, suberic, fumaric, lactic, mandelic, phthalic, benzenesulfonic, p-tolylsulfonic, citric, tartaric, methanesulfonic acid, or the like; and also salts of amino acids (such as arginate and the like), and salts of organic acids like glucuronic acid and the like. Certain specific compounds of embodiments of the invention contain both basic and acidic functionalities that allow the compounds to be converted into either base or acid addition salts.

The term 'excipient' or 'pharmaceutically acceptable excipient' as used herein refers to a component of a pharmaceutical product that is not an active ingredient i.e. does not exhibit pharmacological action. Typical non-limiting examples of excipients include diluents, fillers, waxes, gelling and non-gelling agents, binders, plasticizers, solubilizing agents, wetting agents, suspending agents, flavour enhancers, emulsifying agents and the like. The excipients that are useful in preparing a pharmaceutical composition are generally safe, non-toxic, and neither biologically nor otherwise undesirable, and are acceptable for veterinary use as well as human pharmaceutical use.

In an aspect of embodiments of the invention, there is provided a compound of Formula (I)

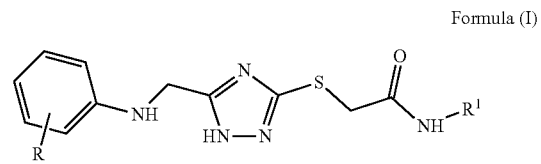

Formula (I)

or a pharmaceutically acceptable salt thereof;
wherein
a) R is hydrogen or $C_1$-$C_6$alkyl, and
b) $R^1$ is aryl or heteroaryl optionally substituted with one or more substituent.

In some embodiments of the invention, there is provided a compound of Formula (I), wherein R is hydrogen or $CH_3$.

In some embodiments of the invention, there is provided a compound of Formula (I), wherein $R^1$ is phenyl or benzthiazolyl optionally substituted with one or more substituent selected from $CH_3$, $OCH_3$, Cl, F, Br, OH, $CONH_2$, $NH_2$, $HNCOCH_3$, $NO_2$, $COCH_3$, $CF_3$ or CN.

In an aspect of embodiments of the invention, there is provided a compound of Formula (II)

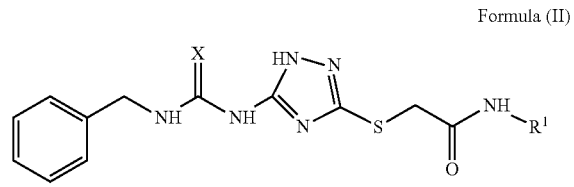

Formula (II)

or a pharmaceutically acceptable salt thereof;
wherein
a) X is O or S, and
b) $R^1$ is aryl or heteroaryl optionally substituted with one or more substituent.

In embodiments of the invention, there is provided a compound of Formula (II), wherein $R^1$ is phenyl optionally substituted with one or substituent selected from $CH_3$, $OCH_3$, Cl, F, Br, OH, $CONH_2$, $NH_2$, $HNCOCH_3$, $NO_2$, $COCH_3$, $CF_3$ or CN.

In embodiments of the invention, there is provided a compound of Formula (II), wherein $R^1$ is benzthiazolyl optionally substituted with one or substituent selected from $CH_3$, $OCH_3$, Cl, F, Br, OH, $CONH_2$, $NH_2$, $HNCOCH_3$, $NO_2$, $COCH_3$, $CF_3$ or CN.

In embodiments of the invention, there is provided a compound of Formula (I) selected from the group comprising of:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;

N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-((5-((m-tolylamino)methyl)-H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide or
a pharmaceutically acceptable salt thereof.

In embodiments of the invention, there is provided a compound of Formula (II) selected from the group comprising of:
2-((5-(3-benzylthioureido)-1H-1,2,4-triazol-3-yl)thio)-N-(5-nitrobenzo[d]thiazol-2-yl)acetamide;
N-(3-acetylphenyl)-2-((5-(3-benzylthioureido)-1H-1,2,4-triazol-3-yl)thio)acetamide;
2-((5-(3-benzylureido)-1H-1,2,4-triazol-3-yl)thio)-N-(4-nitrophenyl)acetamide;
N-(3-acetylphenyl)-2-((5-(3-benzylureido)-1H-1,2,4-triazol-3-yl)thio)acetamide;
2-((5-(3-benzylureido)-1H-1,2,4-triazol-3-yl)thio)-N-(2-methyl-4-nitrophenyl)acetamide
or a pharmaceutically acceptable salt thereof.

In general, there are provided processes for the preparation of compounds according to embodiments of the invention. The compounds of Formula (I) are prepared according to general procedure described in Scheme 1. The compounds of Formula (II) are prepared according to general procedure described in Scheme 2.

In an aspect of embodiments of the invention, there is provided a process for the preparation of a compound of Formula (I), Formula (I)

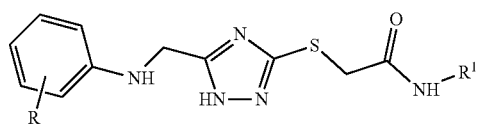

wherein
a) R is hydrogen or $C_1$-$C_6$alkyl, and
b) $R^1$ is aryl or heteroaryl optionally substituted with one or more substituent;

the process comprising steps of:
a) reacting a compound of Formula (A) with ethyl bromoacetate in presence of suitable base and solvent to obtain a compound of Formula (B);

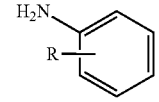

(A)

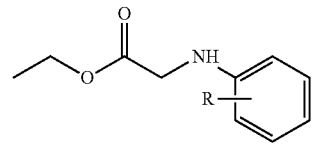

(B)

b) treating the compound of Formula (B) with hydrazine hydrate to obtain a compound of Formula (C);

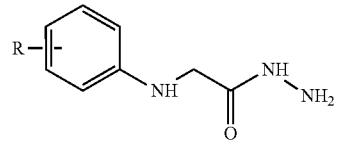

(C)

c) treating the compound of Formula (C) with ammonium formate and thiourea to obtain a compound of Formula (D); and

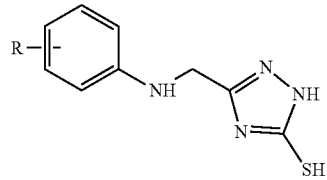

(D)

d) reacting the compound of Formula (D) with substituted α-chloroacetanilide of Formula (H) in the presence of a suitable base to obtain the compound of Formula (I)

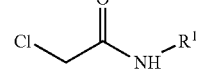

(H)

SCHEME 1

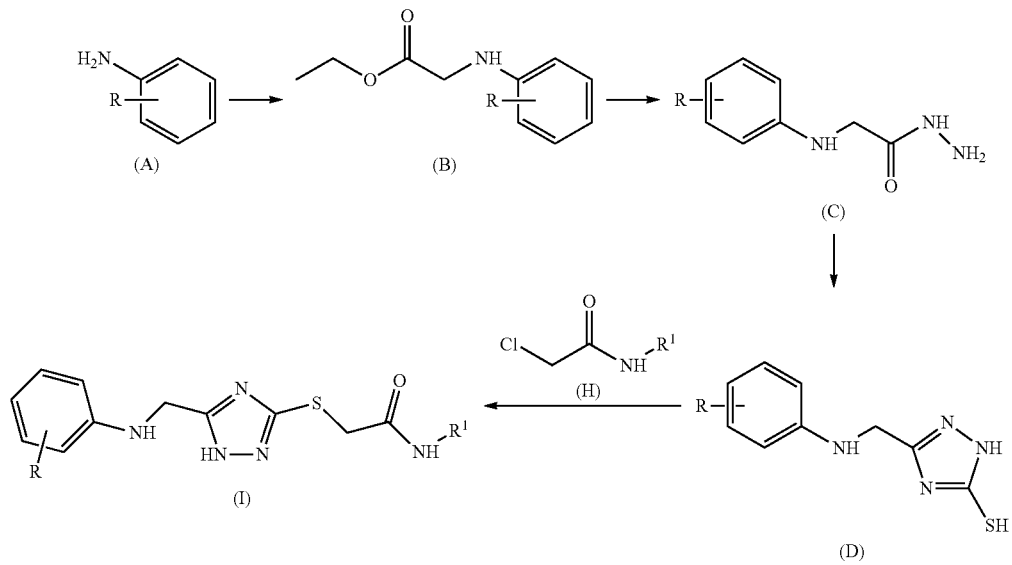

In an aspect of embodiments of the invention, there is provided a process for the preparation of a compound of Formula (II),

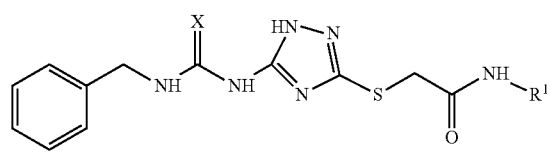
Formula (II)

wherein
a) X is O or S, and
b) R¹ is aryl or heteroaryl optionally substituted with one or more substituent;

the process comprising steps of:
a) reacting a compound of Formula (E) with 3-Amino-1H-1,2,4-triazole-5-thiol of Formula (F) to obtain a compound of Formula (G); and

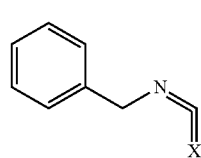
(E)

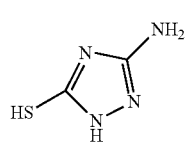
(F)

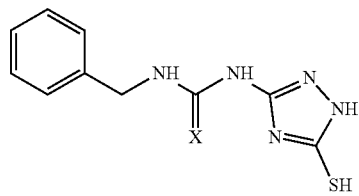
(G)

b) reacting the compound of Formula (G) with substituted α-chloroacetanilide of Formula (H) to obtain a compound of Formula (II)

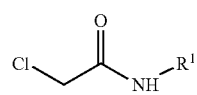
(H)

SCHEME 2

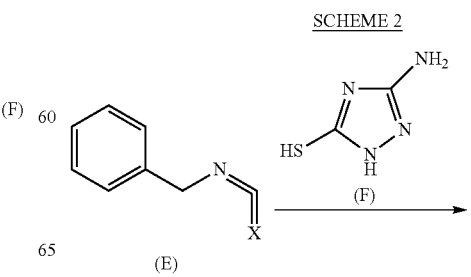

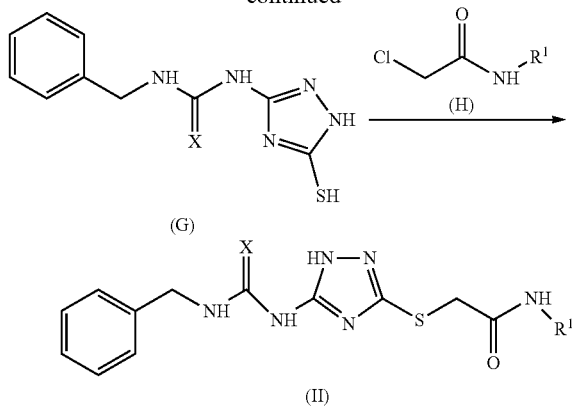

In an aspect of embodiments of the invention, there is provided a pharmaceutical composition for treatment of breast cancer, the composition comprising a compound of Formula (I) or a compound of Formula (II) or a pharmaceutically acceptable salt thereof. In embodiments of the invention, the pharmaceutical composition further comprises one or more pharmaceutically acceptable excipients.

In embodiments, the compositions according to embodiments of the invention are solid compositions for oral administration such as tablets, capsules, powders, granules and the like. In embodiments, the compositions according to embodiments of the invention are liquid compositions for oral administration, of solutions which are pharmaceutically acceptable, suspensions, emulsions, syrups, elixirs and the like. In embodiments, the compositions according to embodiments of the invention are compositions for parenteral administration such as emulsion, suspension, sterile solutions, powder for reconstitution and the like.

In embodiments, the compositions according to embodiments of the invention are compositions for transdermal administration. In embodiments, the compositions according to embodiments of the invention are formulated as transdermal dosage form. In embodiments, the composition according to embodiments of the invention is a transdermal delivery system. The terms 'transdermal delivery system' and 'transdermal dosage form' are interchangeable The term "transdermal" refers to delivery, administration or application of a drug by means of direct contact with skin or mucosa. Some non-limiting examples of transdermal delivery system or transdermal dosage form include creams, ointments, gels, foams, sprays, solutions, lotions (i.e. emulsions, or suspensions), patches and the like. In embodiments, the composition according to invention is a transdermal patch.

In embodiments, the compositions according to embodiments of the invention are formulated as transdermal delivery system comprising pharmaceutically active ingredient (compound of Formula (I) or compound of Formula (II)) and one or more pharmaceutically acceptable excipients selected from dermal penetration enhancer (that is, a material increasing a penetration rate of a drug passing through or penetrating into the skin), a solubilizer (that is, a material effectively solubilizing the drug), tackifier, plasiticizer, or an anti-oxidant.

In embodiments of the invention, there is provided a method for treating breast cancer, the method comprising administering a compound of Formula (I) or a compound of Formula (II) or a pharmaceutically acceptable salt thereof.

In embodiments of the invention, there is provided a method for treating breast cancer, the method comprising administering a pharmaceutical composition comprising a compound of Formula (I) or a compound of Formula (II) or a pharmaceutically acceptable salt thereof.

In some embodiments of the invention there is provided a method for treating breast cancer, the method comprising administering a pharmaceutical composition comprising a compound of Formula (I) or a compound of Formula (II) or a pharmaceutically acceptable salt thereof, wherein the composition is a transdermal delivery system.

In some embodiments, the compounds and compositions of embodiments of the invention are useful in treating triple positive and triple negative types of breast cancers.

In embodiments, the compounds and compositions according to embodiments of the invention act as inhibitors of Cathepsin D enzymes that are involved in downstream regulation of tumor progression and metastasis of breast cancer.

In some embodiments, there is provided a method of treating breast cancer by inhibiting Cathepsin D enzymes, the method comprises administering an effective amount of a compound of formula (I) or a compound of Formula (II) or a pharmaceutically acceptable salt thereof.

In some embodiments, there is provided a method of treating breast cancer by inhibiting Cathepsin D enzymes, the method comprises administering a pharmaceutical composition comprising a compound of formula (I) or a compound of Formula (II) or a pharmaceutically acceptable salt thereof.

In yet other embodiments, the compounds and compositions according to embodiments of the invention exhibit antiangiogenic effect.

In some embodiments, there is provided a method for producing antiangiogenic effect in warm blooded animals such as humans, the method comprises administering a pharmaceutical composition comprising a compound of formula (I) or a compound of Formula (II) or a pharmaceutically acceptable salt thereof.

In embodiments, the compounds of embodiments of the present invention act as inhibitors of Cathepsin D and exhibit antiproliferative activity as well as inhibit angiogenesis. In some embodiments, there is provided a method of exhibiting antiproliferative activity as well as inhibiting angiogenesis, the method comprising administering a compound or composition of embodiments of the present invention.

In embodiments, the compounds and/or compositions according to embodiments of the invention have no acute toxicity profile.

EXAMPLES

All commercially available chemicals and solvents were used without further purification. Melting points of the synthesized compounds were determined by Buchi B-540 open capillary instrument and were uncorrected. The homogeneity of the compounds was monitored by TLC (Thin layer chromatography) on silica gel 40 F254 coated on aluminium plates, visualized by UV or iodine chamber and $KMnO_4$ treatment. All $^1H$ and $^{13}C$ NMR spectra were recorded on a Bruker AM-300 (300.12 MHz, 75.12 MHz) NMR spectrometer and Bruker BioSpin Corp, Germany respectively. Molecular weights of the synthesized compounds were checked by SHIMADZU LCMS-2020 series in ESI mode. Chemical shifts are reported in ppm (δ) with reference to the internal standard TMS. The signals were designated as follows: s, singlet; d, doublet; dd, doublet of doublets; t, triplet; m, multiplet. Elemental analyses were carried out on Elementar Vario MICRO CUBE CHN Analyzer.

PREPARATIVE EXAMPLES

Synthesis of Ethyl 2-(m-tolylamino) acetate: To a stirred solution of m-toluidine (10.0 g, 93.32 mmol and potassium carbonate (32.19 g, 233 mmol) in dimethylformamide (DMF) (100 mL) was added ethyl 2-bromoacetate (18.7 g, 112 mmol) and heated at 110° C. for 16 hour. The reaction was monitored by thin layer chromatography (TLC). After completion of reaction DMF was removed, the crude was diluted with ethylacetate (150 mL), washed with brine (3×100 mL), dried, concentrated obtained crude was purified by flash column chromatography using 20-35% ethyl acetate/petroleum ether to get the titled compound Ethyl 2-(m-tolylamino) acetate as a brown gummy (8.2 g, 45%). ESI-MS was found at m/z 194.43 [M+H]$^+$.

Synthesis of Ethyl 2-(phenylamino) acetate: To a stirred solution of aniline (10.0 g, 107.38 mmol) and potassium carbonate (36.97 g, 267 mmol) in DMF (100 mL) was added ethyl 2-bromoacetate (21.51 g, 128 mmol) and heated at 110° C. for 16 hour. The reaction was monitored by TLC. After completion of reaction DMF was removed, the crude was diluted with ethylacetate (150 ml), washed with brine (3×100 mL), dried, concentrated obtained crude was purified by flash column chromatography using 20-35% ethyl acetate/Petroleum ether to get ethyl 2-(phenylamino) acetate as a brown gummy (7.1 g, 36%). ESI-MS was found at m/z 181.01 [M+H]$^+$.

Synthesis of 2-(m-Tolylamino)acetohydrazide: To a stirred solution of a compound ethyl 2-(m-tolylamino) acetate (6.8 g, 35.19 mmol) in ethanol (100 mL) was added hydrazine hydrate (5.27 g, 105 mmol) and refluxed for 16 hour. The reaction was monitored by TLC. After completion of reaction ethanol was removed; the obtained crude solid was purified bytrituration with diethyl ether and n-pentane to get 2-(m-Tolylamino)acidhydrazide as a pale brown solid (5.7 g, 90%). ESI-MS was found at m/z 181.21 [M+H]$^+$.

Synthesis of 2-(Phenylamino)acetohydrazide: To a stirred solution of compound ethyl 2-(phenylamino) acetate (8 g, 44.64 mmol) in ethanol (100 mL) was added hydrazine hydrate (6.69 g, 134 mmol) and refluxed for 16 hour. The reaction was monitored by TLC. After completion of reaction ethanol was removed, obtained crude solid was purified by triturated with diethyl ether and n-pentane to get 2-(Phenylamino)acetohydrazide as an off-white solid (6.2 g, 84%). ESI-MS was found at m/z 164.41 [M−H]$^+$.

Synthesis of 3-((m-Tolylamino)methyl)-1H-1,2,4-triazole-5-thiol: To a stirred solution of 2-(m-Tolylamino)acidhydrazide (6.0 g, 33.47 mmol) in acetic acid (AcOH) (60 mL) was added ammonium formate (4.2 g, 66.95 mmol), thiourea (5.09 g, 66.95 mmol) and heated at 80° C. for 6 hour. The reaction was monitored by TLC. After completion of reaction AcOH was removed, crushed ice was added and extracted with ethyl acetate (EtOAc) (2×100 mL), obtained crude was purified by flash column chromatography using 70-100% ethyl acetate/petroleum ether to get 3-((m-Tolylamino)methyl)-1H-1,2,4-triazole-5-thiol as a pale yellow solid (5.2 g, 70%). ESI-MS was found at m/z 221.31 [M+H]$^+$.

Synthesis of 3-((Phenylamino)methyl)-1H-1,2,4-triazole-5-thiol: To a stirred solution of 2-(Phenylamino)acetohydrazide (7.0 g, 42.37 mmol) in AcOH (60 mL) was added ammonium formate (5.34 g, 84.75 mmol), thiourea (3.22 g, 42.37 mmol) and heated at 80° C. for 6 hour. The reaction was monitored by TLC. After completion of reaction AcOH was removed, crushed ice was added and extracted with EtOAc (2×100 mL), obtained crude was purified by flash column chromatography using 70-100% ethyl acetate/petroleum ether to get 3-((Phenylamino)methyl)-1H-1,2,4-triazole-5-thiol as a pale yellow solid (5.7 g, 70%). ESI-MS was found at m/z 207.51 [M+H]$^+$.

Synthesis of 1-Benzyl-3-(5-mercapto-1H-1,2,4-triazol-3-yl)thiourea: To a stirred solution of N-benzylthioformamide (1 g, 6.7 mmol) in ethanol (20 mL) was added 3-Amino-1H-1,2,4-triazole-5-thiol (0.778 g, 6.7 mmol) and refluxed for 16 hour. The reaction was monitored by TLC. After completion of reaction ethanol was removed, obtained crude solid was purified by trituration with diethyl ether and n-pentane to get 1-Benzyl-3-(5-mercapto-1H-1,2,4-triazol-3-yl)thiourea as a pale yellow solid (0.92 g, 51%). ESI-MS was found at m/z 264.41 [M−H]$^+$.

Synthesis of 1-Benzyl-3-(5-mercapto-1H-1,2,4-triazol-3-yl)urea: To a stirred solution of N-benzyl formamide (1 g, 7.51 mmol) in ethanol (20 mL) was added 3-Amino-1H-1,2,4-triazole-5-thiol (0.872 g, 7.51 mmol) and refluxed for 16 hour. The reaction was monitored by TLC. After completion of reaction ethanol was removed, obtained solid crude was purified by trituration with diethyl ether and n-pentane to get 1-Benzyl-3-(5-mercapto-1H-1,2,4-triazol-3-yl)urea as an off-white solid (0.9 g, 48%). ESI-MS was found at m/z 250.34 [M+H]$^+$.

General procedure for the synthesis of 1,2,4-triazol-3-yl-thioacetamide derivatives (1-21): To a stirred solution of appropriate above synthesized compound (0.3 g), diisopropylethylamine (DIPEA) (3 equiv) in acetonitrile at 70° C. was added substituted 2-chloroacetanilide compounds (1.3 equiv) in portion wise over a period of 30 minutes. The reaction was monitored by TLC. After completion of reaction acetonitrile was removed, obtained solid crude was purified by flash column chromatography using 60-90% ethyl acetate/petroleum ether (EtOAc/Pet ether) in 100-200 silica gel to get corresponding 1,2,4-triazol-3-yl-thioacetamide derivatives (1-21) in good yields.

Example 1: Synthesis of N-(5-chloro-2-methoxyphenyl)-2-((5-((m-tolylamino)methyl)-1H-1,2,4-triazol-3-yl)thio)acetamide (1)

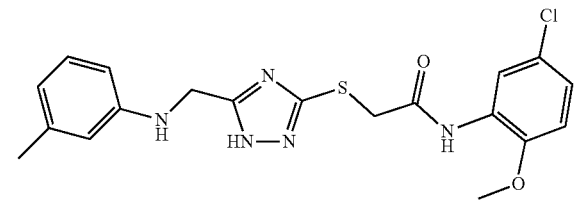 [SMILES: COc1ccc(Cl)cc1NC(=O)CSc1n[nH]c(CNc2cccc(C)c2)n1]

According to the above general procedure to a solution of 3-((m-Tolylamino)methyl)-1H-1,2,4-triazole-5-thiol (0.3 g, 1.36 mmol), DIPEA (0.528 g, 4.08 mmol) in acetonitrile at 70° C. was added 2-chloro-N-(5-chloro-2-methoxyphenyl) acetamide (0.414 g, 1.77 mmol) to get N-(5-chloro-2-methoxyphenyl)-2-((5-((m-tolylamino)methyl)-1H-1,2,4-triazol-3-yl)thio)acetamide as a pale brown solid (0.388 g, 68%); m.p: 40-42° C.; ESI-MS was found at m/z 419.05 [M+H]$^+$; $^1$H NMR (300 MHz, DMSO-d$_6$, TMS): δ$_H$=13.2 (bs, 1H), 7.79 (s, 1H), 7.84 (d, J=7.6 Hz, 1H), 7.61 (d, J=7.7 Hz, 1H), 7.17 (d, J=7.5 Hz, 1H), 7.12 (m, 1H), 6.70-6.51 (m, 3H), 5.1 (s, 1H), 4.31 (s, 2H), 4.11 (s, 2H), 3.84 (s, 3H), 2.33 (s, 3H); and $^{13}$C NMR (DMSO-d$_6$): $\delta_C$=168.3, 160.5 (2C), 147.6 (2C), 140.1, 129.4, 125.7 (2C), 123.2, 118.7, 117.6 (2C), 113.4, 110.3, 55.6, 43.1, 38.4, 21.4.

Example 2: Synthesis of N-Phenyl-2-((5-((m-tolylamino)methyl)-1H-1,2,4-triazol-3-yl)thio)acetamide (2)

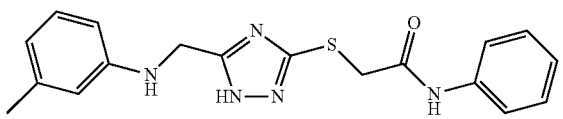 [SMILES: Cc1cccc(NCc2nc(SCC(=O)Nc3ccccc3)n[nH]2)c1]

According to the above general procedure to the solution of 3-((m-Tolylamino)methyl)-1H-1,2,4-triazole-5-thiol (0.3 g, 1.36 mmol), DIPEA (0.528 g, 4.08 mmol) in acetonitrile at 70° C. was added 2-chloro-N-phenyl acetamide (0.3 g, 1.77 mmol) to get N-Phenyl-2-((5-((m-tolylamino)methyl)-1H-1,2,4-triazol-3-yl)thio)acetamide as a pale yellow solid (0.309 g, 64%); m.p: 40-42° C.; ESI-MS was found at m/z 355.10 [M+H]$^+$; $^1$H NMR (300 MHz, DMSO-d$_6$, TMS): $\delta_H$=13.4 (bs, 1H), 7.78 (s, 1H), 7.64-7.10 (m, 6H), 6.65-6.49 (m, 3H), 5.4 (s, 1H), 4.36 (s, 2H), 4.06 (s, 2H), 2.35 (s, 3H). $^{13}$C NMR (DMSO-d$_6$): $\delta_C$=168.1, 160.6 (2C), 147.4, 139.4, 138.7, 129.6, 128.9 (2C), 128.1, 121.4 (2C), 118.0, 113.4, 110.6, 42.6, 38.2 21.5.

Example 3: Synthesis of N-(3-fluorophenyl)-2-((5-((m-tolylamino)methyl)-1H-1,2,4-triazol-3-yl)thio)acetamide (3)

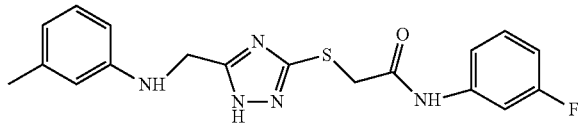 [SMILES: Cc1cccc(NCc2nc(SCC(=O)Nc3cccc(F)c3)n[nH]2)c1]

According to the above general procedure to a solution of 3-((m-tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(4-fluorophenyl)acetamide (0.35 g, 1.77 mmol) to get N-Phenyl-2-((5-((m-tolylamino)methyl)-1H-1,2,4-triazol-3-yl)thio)acetamide as a pale yellow solid (0.330 g, 65%); m.p: 40-42° C.; ESI-MS was found at m/z 373.05 [M+H]$^+$; $^1$H NMR (300 MHz, DMSO-d$_6$, TMS): $\delta$=13.3 (bs, 1H), 7.80 (s, 1H), 7.76-7.10 (m, 4H), 6.97 (m, 1H), 6.67-6.50 (m, 3H), 5.5 (s, 1H), 4.34 (s, 2H), 4.04 (s, 2H), 2.33 (s, 3H). $^{13}$C NMR (DMSO-d$_6$): $\delta_C$=168.3, 163.4, 159.6 (2C), 147.4, 140.2, 139.4, 130.7, 129.4, 117.5 (2C), 116.2 (2C), 113.6, 110.4, 42.5, 38.5, 21.4.

Example 4: Synthesis of N-(3-bromophenyl)-2-((5-((m-tolylamino)methyl)-1H-1,2,4-triazol-3-yl)thio)acetamide (4)

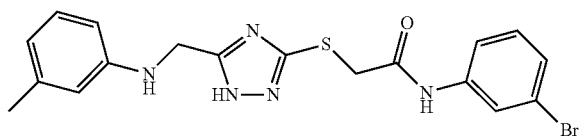 [SMILES: Cc1cccc(NCc2nc(SCC(=O)Nc3cccc(Br)c3)n[nH]2)c1]

According to the above general procedure to the solution of 3-((m-Tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(3-bromophenyl) acetamide (0.440 g, 1.77 mmol) to get N-(3-bromophenyl)-2-((5-((m-tolylamino)methyl)-1H-1,2,4-triazol-3-yl)thio) acetamide as a pale yellow solid (0.336 g, 57%); m.p: 40-42° C.; ESI-MS was found at m/z 435.00 [M+2]$^+$; $^1$H NMR (300 MHz, DMSO-d$_6$, TMS): $\delta_H$=13.4 (bs, 1H), 7.82 (s, 1H), 7.88 (m, 1H), 7.36-7.09 (m, 4H), 6.67-6.51 (m, 3H), 5.6 (s, 1H), 4.33 (s, 2H), 4.05 (s, 2H), 2.35 (s, 3H); and $^{13}$C NMR (DMSO-d$_6$): $\delta_C$=168.4, 160.5 (2C), 147.6, 140.8, 139.3, 130.1 (2C), 127.2, 123.5, 120.8 (2C), 117.6, 113.4, 110.5, 42.6, 38.2 21.2.

Example 5: Synthesis of N-(4-methoxyphenyl)-2-((5-((m-tolylamino)methyl)-1H-1,2,4-triazol-3-yl)thio)acetamide (5)

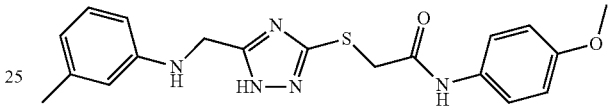

According to the above general procedure to the solution of 3-((m-Tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(4-methoxyphenyl) acetamide (0.353 g, 1.77 mmol) to get N-(4-methoxyphenyl)-2-((5-((m-tolylamino)methyl)-1H-1,2,4-triazol-3-yl) thio)acetamide as a pale brown solid (0.335 g, 64%); m.p: 40-42° C.; ESI-MS was found at m/z 385.41 [M+H]$^+$; $^1$H NMR (300 MHz, DMSO-d$_6$, TMS): $\delta_H$=13.5 (bs, 1H), 7.83 (s, 1H), 7.54 (d, J=7.6 Hz, 2H), 7.13 (m, 1H), 6.98 (d, J=7.7 Hz, 2H), 6.67-6.51 (m, 3H), 5.6 (s, 1H), 4.31 (s, 2H), 4.04 (s, 2H), 3.84 (s, 3H), 2.32 (s, 3H). 168.3, 160.4 (2C). $^{13}$C NMR (DMSO-d$_6$): $\delta$C=160.0, 147.7, 139.3, 130.7, 129.6, 122.6 (2C), 120.8 (2C), 117.4, 114.6 (2C), 113.3, 110.4, 56.0, 42.4, 38.7 21.5.

Example 6: Synthesis of N-(3,4-dichlorophenyl)-2-((5-((m-tolylamino)methyl)-1H-1,2,4-triazol-3-yl)thio)acetamide (6)

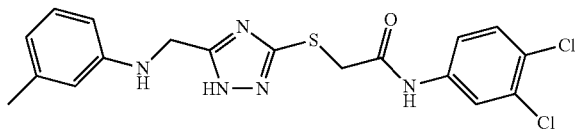 [SMILES: Cc1cccc(NCc2nc(SCC(=O)Nc3ccc(Cl)c(Cl)c3)n[nH]2)c1]

According to the above general procedure to the solution of 3-((m-Tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(3,4-dichlorophenyl) acetamide (0.42 g, 1.77 mmol) to get N-(3,4-dichlorophenyl)-2-((5-((m-tolylamino)methyl)-1H-1,2,4-triazol-3-yl) thio)acetamide as a pale brown solid (0.381 g, 66%); m.p: 40-42° C.; ESI-MS was found at m/z 423.00 [M]$^+$; $^1$H NMR (300 MHz, DMSO-d$_6$, TMS): $\delta_H$=13.7 (bs, 1H), 8.01 (s, 1H), 7.89 (m, 1H), 7.65-7.11 (m, 3H), 6.67-6.52 (m, 3H), 5.61 (s, 1H), 4.33 (s, 2H), 4.06 (s, 2H), 2.33 (s, 3H); and $^{13}$C NMR (DMSO-d$_6$): δ$_C$=168.2, 160.3 (2C), 147.6, 139.5, 138.1, 130.6, 131.3, 129.2 (2C), 124.6, 120.9, 117.6, 113.4, 110.6, 42.6, 38.8, 21.5.

Example 7: Synthesis of N-(3,5-dimethoxyphenyl)-2-((5-((m-tolylamino)methyl)-1H-1,2,4-triazol-3-yl)thio)acetamide (7)

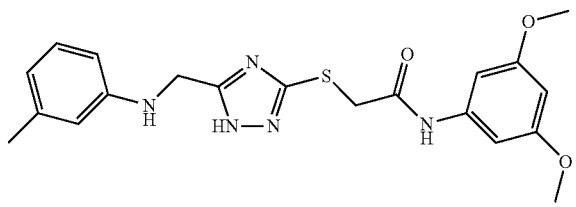

According to the above general procedure to the solution of 3-((m-Tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(3,5-dimethoxyphenyl) acetamide (0.407 g, 1.77 mmol) to get N-(3,5-dimethoxyphenyl)-2-((5-((m-tolylamino)methyl)-1H-1,2,4-triazol-3-yl)thio)acetamide as a pale yellow solid (0.339 g, 60%); m.p: 40-42° C.; ESI-MS was found at m/z 415.61 [M+H]$^+$; $^1$H NMR (300 MHz, DMSO-d$_6$, TMS): δ$_H$=13.6 (bs, 1H), 7.86 (s, 1H), 7.11 (m, 1H), 6.93 (m, 2H), 6.65-6.51 (m, 3H), 6.13 (m, 1H), 5.63 (s, 1H), 4.35 (s, 2H), 4.04 (s, 2H), 3.84 (s, 6H), 2.35 (s, 3H). 168.5, 160.6 (2C); and $^{13}$C NMR (DMSO-d$_6$): δ$_C$=160.0 (2C), 147.4, 140.6, 139.4, 130.2, 117.5, 113.6, 110.4, 102.6 (2C), 42.4, 38.6, 21.2.

Example 8: Synthesis of N-(2-chloro-5-(trifluoromethyl)phenyl)-2-((5-((m-tolylamino)methyl)-1H-1,2,4-triazol-3-yl)thio)acetamide (8)

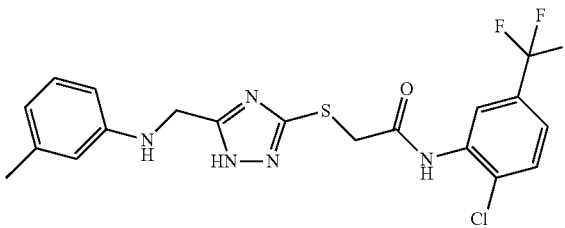

According to the above general procedure to the solution of 3-((m-Tolylamino)methyl)-1H-1,2,4-triazole-5-thiol (0.3 g, 1.36 mmol) and DIPEA (0.528 g, 4.08 mmol) in acetonitrile at 70° C. was added 2-chloro-N-(2-chloro-5-trifluoromethylphenyl) acetamide (0.50 g, 1.77 mmol) to get N-(2-chloro-5-(trifluoromethyl)phenyl)-2-((5-((m-tolylamino)methyl)-1H-1,2,4-triazol-3-yl)thio) acetamide as a brown solid (0.342 g, 55%); m.p: 40-42° C.; ESI-MS was found at m/z 455.05 [M−H]$^-$; $^1$H NMR (300 MHz, DMSO-d$_6$, TMS): δ$_H$=13.2 (bs, 1H), 8.16 (s, 1H), 8.01 (1, H), 7.41-7.10 (m, 3H), 6.66-6.53 (m, 3H), 5.61 (s, 1H), 4.33 (s, 2H), 4.06 (s, 2H), 2.33 (s, 3H); $^{13}$C NMR (DMSO-d$_6$): δ$_C$=168.4, 160.5 (2C), 147.6, 140.0, 137.5, 129.4 (3C), 126.1, 124.2, 122.0, 118.9, 117.7, 113.4, 110.4, 42.6, 38.4, 21.6.

Example 9: Synthesis of N-phenyl-2-((5-((phenylamino)methyl)-1H-1,2,4-triazol-3-yl)thio)acetamide (9)

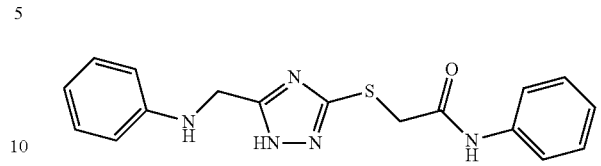

According to the above general procedure to the solution of 3-((Phenylamino)methyl)-1H-1,2,4-triazole-5-thiol (0.28 g, 1.36 mmol), DIPEA (0.563 g, 4.36 mmol) in acetonitrile at 70° C. was added 2-chloro-N-phenyl acetamide (0.30 g, 1.77 mmol) to get N-phenyl-2-((5-((phenylamino)methyl)-1H-1,2,4-triazol-3-yl)thio)acetamide as a pale brown solid (0.292 g, 59%); m.p: 40-42° C.; ESI-MS was found at m/z 339.23 [M−H]$^-$; $^1$H NMR (300 MHz, DMSO-d$_6$, TMS): δ$_H$=13.2 (bs, 1H), 7.79 (s, 1H), 7.64-7.21 (m, 7H), 6.85-6.75 (m, 3H), 5.46 (s, 1H), 4.35 (s, 2H), 4.05 (s, 2H); and $^{13}$C NMR (DMSO-d$_6$): δ$_C$=168.2, 160.5 (2C), 147.4, 139.3, 138.6, 129.4, 128.8 (2C), 128.0, 121.4 (2C), 118.1, 113.5, 110.5, 42.4, 38.3.

Example 10: Synthesis of N-(3-fluorophenyl)-2-((5-((phenylamino)methyl)-1H-1,2,4-triazol-3-yl)thio)acetamide (10)

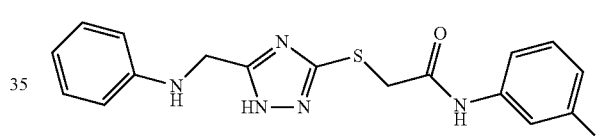

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(3-fluorophenyl) acetamide (0.355 g, 1.77 mmol) to get N-(3-fluorophenyl)-2-((5-((phenylamino)methyl)-1H-1,2,4-triazol-3-yl)thio) acetamide as a yellow solid (0.297 g, 57%); m.p: 40-42° C.; ESI-MS was found at m/z 359.45 [M+H]$^+$; $^1$H NMR (300 MHz, DMSO-d$_6$, TMS): δ$_H$=13.6 (bs, 1H), 7.81 (s, 1H), 7.77-7.11 (m, 4H), 6.99 (m, 1H), 6.66-6.49 (m, 3H), 5.53 (s, 1H), 4.35 (s, 2H), 4.05 (s, 2H); and $^{13}$C NMR (DMSO-d$_6$): δ$_C$=168.4, 163.6, 159.4 (2C), 147.5, 140.4, 139.2, 130.8, 129.3, 117.4 (2C), 116.4 (2C), 113.5, 110.6, 42.6.

Example 11: Synthesis of N-(3-bromophenyl)-2-((5-((phenylamino)methyl)-1H-1,2,4-triazol-3-yl)thio)acetamide (11)

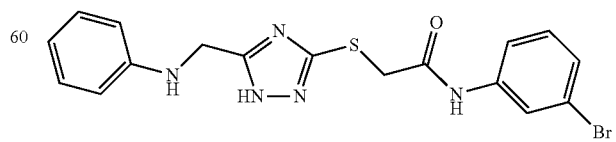

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(3-bromophenyl) acetamide (0.44 g, 1.77 mmol) to get N-(3-bromophenyl)-2-((5-((phenylamino)methyl)-1H-1,2,4-triazol-3-yl)thio) acetamide as a pale yellow solid (0.335 g, 55%); m.p: 40-42° C.; ESI-MS was found at m/z 418.00 [M–H]$^-$; $^1$H NMR (300 MHz, DMSO-d$_6$, TMS): $\delta_H$=13.3 (bs, 1H), 7.83 (s, 1H), 7.89 (m, 1H), 7.38-7.08 (m, 4H), 6.66-6.50 (m, 3H), 5.62 (s, 1H), 4.32 (s, 2H), 4.06 (s, 2H); and $^{13}$C NMR (DMSO-d$_6$): $\delta_C$=168.3, 160.4 (2C), 149.6, 140.6, 139.8, 130.0 (2C), 127.3, 123.7, 120.7 (3C), 113.4 (2C), 42.4, 38.6.

Example 12: Synthesis of N-(4-methoxyphenyl)-2-((5-((phenylamino)methyl)-1H-1,2,4-triazol-3-yl)thio)acetamide (12)

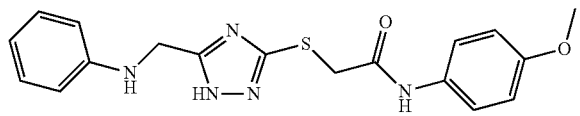 [SMILES: COc1ccc(NC(=O)CSc2n[nH]c(CNc3ccccc3)n2)cc1]

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(4-methoxyphenyl) acetamide (0.35 g, 1.77 mmol) to get N-(4-methoxyphenyl)-2-((5-((phenylamino)methyl)-1H-1,2,4-triazol-3-yl)thio)acetamide as a pale brown solid (0.323, 60%); m.p: 40-42° C.; ESI-MS was found at m/z 371.05 [M+H]$^+$; $^1$H NMR (300 MHz, DMSO-d$_6$, TMS): $\delta_H$=13.2 (bs, 1H), 7.85 (s, 1H), 7.52 (d, J=7.7 Hz, 2H), 7.23 (m, 2H), 6.98 (d, J=7.7 Hz, 2H), 6.87-6.71 (m, 3H), 5.32 (s, 1H), 4.35 (s, 2H), 4.05 (s, 2H), 3.84 (s, 3H); $^{13}$C NMR (DMSO-d$_6$): $\delta_C$=168.4, 160.4 (2C), 159.6, 149.7, 130.9, 129.4 (2C), 122.6 (2C), 120.8, 114.7 (2C), 113.6 (2C), 56.1, 42.5, 38.4.

Example 13: Synthesis of N-(3,4-dichlorophenyl)-2-((5-((phenylamino)methyl)-1H-1,2,4-triazol-3-yl)thio)acetamide (13)

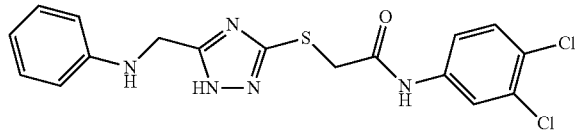 [SMILES: O=C(CSc1n[nH]c(CNc2ccccc2)n1)Nc1ccc(Cl)c(Cl)c1]

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(3,4-dichlorophenyl) acetamide (0.42 g, 1.77 mmol) to get N-(3,4-dichlorophenyl)-2-((5-((phenylamino)methyl)-1H-1,2,4-triazol-3-yl)thio)acetamide as a yellow solid (0.339 g, 57%); m.p: 40-42° C.; ESI-MS was found at m/z 408.00 [M–H]$^-$; $^1$H NMR (300 MHz, DMSO-d$_6$, TMS): $\delta_H$=13.4 (bs, 1H), 7.99 (s, 1H), 7.92 (m, 1H), 7.65-7.50 (m, 2H), 7.23 (m, 2H), 6.79-6.81 (m, 3H), 5.63 (s, 1H), 4.36 (s, 2H), 4.03 (s, 2H); and $^{13}$C NMR (DMSO-d$_6$): $\delta_C$=168.4, 160.5 (2C), 149.6, 138.1, 131.4, 130.4, 129.6 (2C), 128.9, 124.5, 121.0 (2C), 113.7 (2C), 42.4, 38.6.

Example 14: Synthesis of N-(3,5-dimethoxyphenyl)-2-((5-((phenylamino)methyl)-1H-1,2,4-triazol-3-yl)thio)acetamide (14)

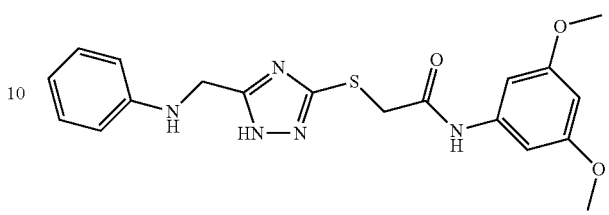

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(3,5-dimethoxyphenyl) acetamide (0.40 g, 1.77 mmol) to get N-(3,5-dimethoxyphenyl)-2-((5-((phenylamino)methyl)-1H-1,2,4-triazol-3-yl)thio)acetamide as a pale yellow solid (0.315 g, 54%); m.p: 40-42° C.; ESI-MS was found at m/z 401.10 [M+H]$^+$; $^1$H NMR (300 MHz, DMSO-d$_6$, TMS): $\delta_H$=13.3 (bs, 1H), 7.83 (s, 1H), 7.21 (m, 2H), 6.95 (m, 2H), 6.85-6.75 (m, 3H), 6.10 (m, 1H), 5.66 (s, 1H), 4.37 (s, 2H), 4.06 (s, 2H), 3.85 (s, 6H); and $^{13}$C NMR (DMSO-d$_6$): $\delta_C$=168.4, 160.5 (2C), 160.0 (2C), 149.4, 140.5, 130.1 (2C), 120.6, 113.6 (2C), 102.4 (2C), 96.1, 42.6, 38.4.

Example 15: Synthesis of N-(2-chloro-5-(trifluoromethyl)phenyl)-2-((5-((phenylamino)methyl)-1H-1,2,4-triazol-3-yl)thio)acetamide (15)

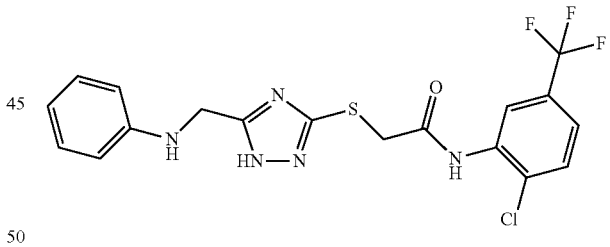

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(2-chloro-5-trifluoromethylphenyl) acetamide (0.50 g, 1.77 mmol) to get N-(2-chloro-5-(trifluoromethyl)phenyl)-2-((5-((phenylamino)methyl)-1H-1,2,4-triazol-3-yl)thio)acetamide as a brown solid (0.338 g, 55%); m.p: 40-42° C.; ESI-MS was found at m/z 455.10 [M+MeOH]$^+$; $^1$H NMR (300 MHz, DMSO-d$_6$, TMS): $\delta_H$=13.4 (bs, 1H), 8.13 (s, 1H), 8.03 (1, H), 7.41-7.20 (m, 4H), 6.86-6.73 (m, 3H), 5.63 (s, 1H), 4.35 (s, 2H), 4.04 (s, 2H); and $^{13}$C NMR (DMSO-d$_6$): $\delta_C$=168.4, 160.5 (2C), 149.6, 137.7, 129.7 (2C), 126.3 (2C), 125.8, 124.2, 122.2, 120.7, 118.9, 113.4 (2C), 42.6, 38.6.

Example 16: Synthesis of N-(5-chloro-2-methoxyphenyl)-2-((5-((phenylamino)methyl)-1H-1,2,4-triazol-3-yl)thio)acetamide (16)

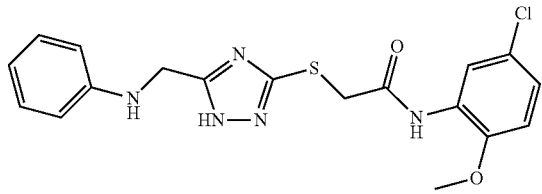 [SMILES: COc1ccc(Cl)cc1NC(=O)CSc1n[nH]c(CNc2ccccc2)n1]

According to the above general procedure, to the solution of 3-((Phenylamino)methyl)-1H-1,2,4-triazole-5-thiol (0.28 g, 1.36 mmol) and DIPEA (0.563 g, 4.36 mmol) in acetonitrile at 70° C. was added 2-chloro-N-(5-chloro-2-methoxyphenyl) acetamide (0.414 g, 1.77 mmol) to get N-(5-chloro-2-methoxyphenyl)-2-((5-((phenylamino)methyl)-1H-1,2,4-triazol-3-yl)thio)acetamide as a pale yellow gum (0.342 g, 58%); ESI-MS was found at m/z 403.73 [M−H]−; $^1$H NMR (300 MHz, DMSO-d$_6$, TMS): $\delta_H$=13.3 (bs, 1H), 7.81 (s, 1H), 7.84 (m, 1H), 7.60 (d, J=7.7 Hz, 1H), 7.24 (m, 2H), 7.17 (d, J=7.5 Hz, 1H), 6.83-6.71 (m, 3H), 5.2 (s, 1H), 4.35 (s, 2H), 4.06 (s, 2H), 3.84 (s, 3H); and $^{13}$C NMR (DMSO-d$_6$): $\delta_C$=168.3, 160.5 (2C), 149.4, 147.6, 129.4 (2C), 126.5 (2C), 123.1, 120.6, 118.7, 117.5, 113.6 (2C), 55.6, 42.5, 38.6.

Example 17: Synthesis of 2-((5-(3-benzylthioureido)-1H-1,2,4-triazol-3-yl)thio)-N-(5-nitrobenzo[d]thiazol-2-yl)acetamide (17)

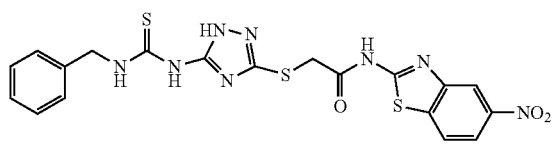 [SMILES: O=C(CSc1n[nH]c(NC(=S)NCc2ccccc2)n1)Nc1nc2cc([N+](=O)[O-])ccc2s1]

According to the above general procedure, to the solution of 1-benzyl-3-(3-sulfanyl-1H-1,2,4-triazol-5-yl)thiourea (0.36 g, 1.36 mmol), DIPEA (0.563 g, 4.36 mmol) in acetonitrile at 70° C. was added 2-chloro-N-(5-nitro-1,3-benzo[d]thiazol-2-yl) acetamide (0.48 g, 1.77 mmol) to get 2-((5-(3-benzylthioureido)-1H-1,2,4-triazol-3-yl)thio)-N-(5-nitrobenzo[d]thiazol-2-yl)acetamide as a pale browngum (0.323 g, 57%); ESI-MS was found at m/z 501.51 [M+H]+; $^1$H NMR (300 MHz, DMSO-d$_6$, TMS): $\delta_H$=13.5 (bs, 1H), 9.18 (s, 1H), 9.15 (m, 1H), 8.35-8.25 (m, 4H), 7.36-7.21 (m, 5H), 4.68 (s, 2H), 4.06 (s, 2H); and $^{13}$C NMR (DMSO-d$_6$): $\delta_C$=179.6, 174.8, 168.3, 160.5, 154.6, 150.1, 146.4, 138.1, 136.8, 128.6 (2C), 126.8 (3C), 123.0, 120.2, 117.5, 50.9, 38.6.

Example 18: Synthesis of N-(3-acetylphenyl)-2-((5-(3-benzylthioureido)-1H-1,2,4-triazol-3-yl)thio)acetamide (18)

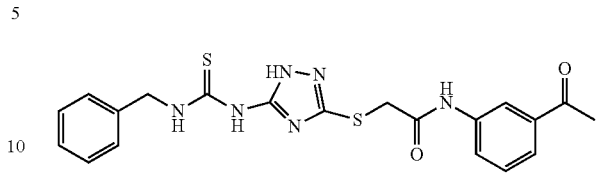

According to the above general procedure by using compound 1-benzyl-3-(3-sulfanyl-1H-1,2,4-triazol-5-yl) thiourea (0.30 g, 1.13 mmol), DIPEA (0.438 g, 3.39 mmol) in acetonitrile at 70° C. was added 2-chloro-N-(3-acetylphenyl) acetamide (0.311 g, 1.47 mmol) to get N-(3-acetylphenyl)-2-((5-(3-benzylthioureido)-1H-1,2,4-triazol-3-yl)thio)acetamide as a pale yellow solid (0.279 g, 56%); m.p: 40-42° C.; ESI-MS was found at m/z 441.31 [M+H]+; $^1$H NMR (300 MHz, DMSO-d$_6$, TMS): $\delta_H$=13.1 (bs, 1H), 9.15 (m, 1H), 8.28 (s, 1H), 8.15 (m, 1H), 7.88-7.25 (m, 8H), 5.23 (s, 1H), 4.75 (s, 2H), 4.02 (s, 2H), 2.6 (s, 3H); and $^{13}$C NMR (DMSO-d$_6$): $\delta_C$=198.0, 179.6, 168.3, 160.5, 154.6, 141.3, 138.0, 136.8, 133.4, 128.7 (2C), 126.7 (3C), 126.1, 124.6, 118.5, 50.7, 38.7, 26.8.

Example 19: Synthesis of 2-((5-(3-benzylureido)-1H-1,2,4-triazol-3-yl)thio)-N-(4-nitrophenyl)acetamide (19)

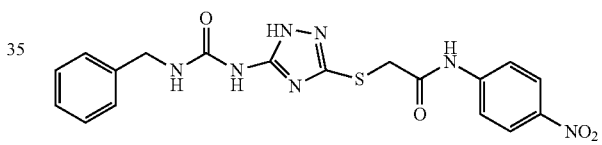

According to the above general procedure by using compound 1-benzyl-3-(3-sulfanyl-1H-1,2,4-triazol-5-yl) urea (0.28 g, 1.13 mmol), DIPEA (0.438 g, 3.39 mmol) in acetonitrile at 70° C. was added 2-chloro-N-(4-nitrophenyl) acetamide (0.315 g, 1.47 mmol) to get 2-((5-(3-benzylureido)-1H-1,2,4-triazol-3-yl)thio)-N-(4-nitrophenyl)acetamide as a pale brown solid (0.273 g, 53%); m.p: 40-42° C.; ESI-MS was found at m/z 428.21 [M+H]+; $^1$H NMR (300 MHz, DMSO-d$_6$, TMS): $\delta_H$=13.4 (bs, 1H), 9.15 (s, 1H), 8.28 (s, 1H), 8.25 (d, J=7.8 Hz, 2H), 7.85 (d, J=7.8 Hz, 2H), 7.38-7.25 (m, 5H), 5.23 (s, 1H), 4.27 (s, 2H), 4.06 (s, 2H); and $^{13}$C NMR (DMSO-d$_6$): $\delta_C$=170.1, 160.3, 154.6, 154.2, 144.8, 143.5, 137.7, 128.6 (2C), 126.8 (3C), 124.2 (2C), 119.8 (2C), 44.6, 38.6.

Example 20 Synthesis of N-(3-acetylphenyl)-2-((5-(3-benzylureido)-1H-1,2,4-triazol-3-yl)thio)acetamide (20)

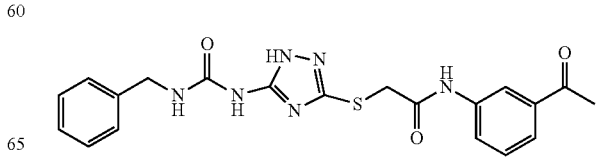

According to the above general procedure by using compound 1-benzyl-3-(3-sulfanyl-1H-1,2,4-triazol-5-yl) urea (0.30 g, 1.20 mmol) and DIPEA (0.528 g, 4.08 mmol) in acetonitrile at 70° C. was added 2-chloro-N-(3-acetylphenyl) acetamide (0.331 g, 1.56 mmol) to get N-(3-acetylphenyl)-2-((5-(3-benzylureido)-1H-1,2,4-triazol-3-yl)thio)acetamide as a yellow solid (0.286 g, 56%); m.p: 40-42° C.; ESI-MS was found at m/z 425.23 [M+H]+; 1H NMR (300 MHz, DMSO-d6, TMS): δ$_H$=13.4 (bs, 1H), 8.55 (m, 1H), 8.25 (s, 1H), 8.16 (m, 1H), 7.88-7.25 (m, 8H), 5.26 (s, 1H), 4.35 (s, 2H), 4.07 (s, 2H), 2.62 (s, 3H); and 13C NMR (DMSO-d6): δ$_C$=198.0, 168.3, 160.5, 154.6 (2C), 141.3, 138.1, 137.0, 133.4, 128.6 (2C), 126.8 (3C), 126.0, 124.5, 118.5, 44.6, 38.6, 26.4.

Example 21: Synthesis of 2-((5-(3-benzylureido)-1H-1,2,4-triazol-3-yl)thio)-N-(2-methyl-4-nitrophenyl)acetamide (21)

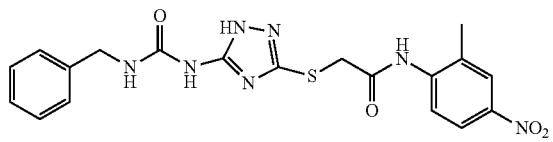 [SMILES: Cc1cc([N+](=O)[O-])ccc1NC(=O)CSc1n[nH]c(NC(=O)NCc2ccccc2)n1]

According to the above general procedure by using 1-benzyl-3-(3-sulfanyl-1H-1,2,4-triazol-5-yl) urea (0.30 g, 1.20 mmol) and DIPEA (0.528 g, 4.08 mmol) in acetonitrile at 70° C. was added 2-chloro-N-(2-methyl-4-nitrophenyl) acetamide (0.358 g, 1.56 mmol) to get 2-((5-(3-benzylureido)-1H-1,2,4-triazol-3-yl)thio)-N-(2-methyl-4-nitrophenyl)acetamide as a pale brown solid (0.292 g, 55%); m.p: 40-42° C.; ESI-MS was found at m/z 440.12 [M−H]−; 1H NMR (300 MHz, DMSO-d6, TMS): δ$_H$=13.3 (bs, 1H), 8.53 (s, 1H), 8.25 (s, 1H), 8.12-8.06 (m, 2H), 7.76-7.25 (m, 6H), 5.26 (s, 1H), 4.26 (s, 2H), 4.07 (s, 2H), 2.12 (s, 3H); and 13C NMR (DMSO-d6): δ$_C$=168.3, 160.5, 154.6 (2C), 143.6, 142.3, 138.1, 135.3, 128.5 (2C), 126.8 (3C), 125.7, 121.2, 108.5, 44.6, 38.6, 16.4.

Biological Assay

An enzyme assay was performed to test the inhibitory effect of compounds of Formula (I) and Formula (II) against Cathepsin D and in cell-based assays on a panel of breast cancer cells including triple positive and triple negative types of breast cancers. Both types of breast cancers were selected with confirmed for their Cathepsin D gene expression using Real Time Polymerase Chain Reaction (RT-PCR) analyses. Also, growth inhibition studies were carried on MCF-7, MDA-MB-231, SK-BR-3, MDA-MB-468 panel of breast cancer cell lines and cytotoxicity studies on HEK293T (human normal cells) using MTT assay. Cells lines were procured from American Type Culture Collection, Manassas, Va., USA and processed according to ATCC protocols. They were cultured in media supplemented with 10% new born calf serum, along with 1% non-essential amino acids, 0.2% sodium bicarbonate, 1% sodium pyruvate and 1% antibiotic mixture (10000 U penicillin and 10 mg streptomycin per mL). Cell lines were maintained at 37° C. in a humidified 5% CO2 incubator (Thermo scientific). Cell lines were processed by initial trypsinization to detach the adhered cells and followed by centrifugation to get cell pellet. Fresh media was added to the pellet to make a cell count using haemocytometer and plate 100 μL of media with cells ranging from 5,000-6,000 per well in a 96-well plate. The plate was incubated overnight in CO2 incubator for the cells to adhere and regain their shape. After 24 hours cells were treated with the novel compounds of Formula (I) at various concentrations ranging from 100 μM-0.1 nM diluted using the media to attain <1% DMSO in the wells. The cells were incubated for 48-72 hour depending on the doubling time of the cell line. Zero hour reading was noted down with untreated cells and also control with 1% DMSO to subtract further from the final reading.

After 48-72 hour incubation, cells were treated with MTT (4, 5-dimethylthiazol-2-yl)-2, 5-diphenyltetrazolium bromide) dissolved in Phosphate Buffer Saline (5 mg/ml) and incubated for 3-4 hour at 37° C. The formazan crystals thus formed were dissolved in 100 μL of DMSO and the viability was measured at 540 nm on a multimode reader (Spectra max).

The compounds of Formula (I), compounds of Formula (II) and its analogues showed significant inhibitory activity towards Cathepsin D and also in reducing the growth of breast cancer cells. The novel compounds of Formula (I), compounds of Formula (II) and analogues of embodiments of the present invention are useful as inhibitors of Cathepsin D enzyme and are involved in down-regulation of tumor progression and metastasis of breast cancer. The novel compounds are seen to be effective against triple positive and triple negative breast cancer cell lines and hence would be effective in the treatment of breast cancer. The compounds have a high selectivity towards the target i.e. Cathepsin D and hence would have a lesser toxicity profile as compared to other available anti-cancer drugs.

Further, Growth Inhibitory Concentration (GIC$_{50}$) and Cytostatic Concentration (CC$_{50}$) were calculated to establish biological activity of the compound of Formula (I) and (II); and the GIC$_{50}$ ranged from 0.47 μM to 97 μM and the CC$_{50}$ were >100 μM for most of the compounds.

The compounds according to embodiments of the invention have shown significant inhibitory activity towards Cathepsin D and were also effective in reducing the growth of breast cancer cells. The compounds showed inhibitory potential against a panel of breast cancer cell lines that included triple positive (ER, PR and HER2), Her2 negative and Triple negative breast cancer cell lines. The compounds were effective against the panel of breast cancer cell lines with 50% growth inhibition between 0.47 μM-20 μM and non-toxic at the active concentration which was proved with their 50% cytotoxic concentration ranging from 0.47 μM to 97 μM.

The compounds according to embodiments of the invention were tested for acute toxicity and were found to be non-lethal up to 2 gm/kg in-vivo. The compounds according to embodiments of the invention were also proven to be anti-angiogenic as revealed by its activity in a zebra fish model and based on the gene suppression of VEGF, MMPs etc.

The skin permeability studies for representative compounds of Formula (I), compounds of Formula (II) and analogues was studied in porcine ear skin in-vitro at various concentration for 48 hour and was found to be successful in delivering transdermally from 6-10 mg/day through skin with various patch sizes.

Thus, the compounds of embodiments of the present invention exhibited the inhibitory activity against Cathepsin D enzymes which are involved in downstream regulation of tumor progression and metastasis of breast cancer.

Although the invention has been illustrated and described in greater detail with reference to the preferred exemplary embodiments, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

I claim:

1. A compound,
wherein the compound is selected from the group consisting of:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;
N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-(5-((m-tolylamino)methyl)-1H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide; and
a pharmaceutically acceptable salt thereof.

2. A process for the preparation of a compound,
wherein the compound is selected from the group consisting of:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;
N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-((5-((m-tolylamino)methyl)-1H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide; and
a pharmaceutically acceptable salt thereof;
wherein
the process comprises:
a) reacting a compound of Formula (A) with ethyl bromoacetate in presence of a base and a solvent to obtain a compound of Formula (B), wherein R is hydrogen or a CH$_3$;

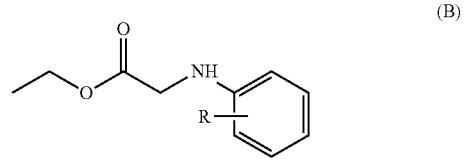

b) treating the compound of Formula (B) with hydrazine hydrate to obtain a compound of Formula (C);

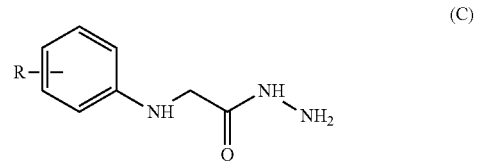

c) treating the compound of Formula (C) with ammonium formate and thiourea to obtain a compound of Formula (D); and

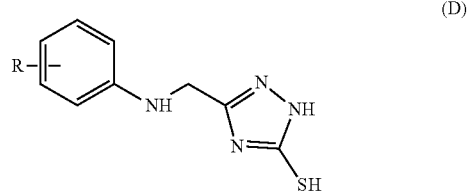

d) reacting the compound of Formula (D) with substituted α-chloroacetanilide of Formula (H), wherein R$^1$ is phenyl or benzthiazolyl optionally substituted with one or more substituents selected from CH$_3$, OCH$_3$, Cl, F, Br, OH, CONH$_2$, NH$_2$, HNCOCH$_3$, NO$_2$, COCH$_3$, COOH, CF$_3$, and CN,

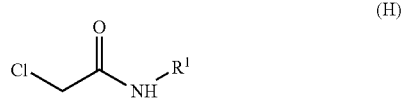

(H)

in the presence of a base to obtain the compound.

3. A pharmaceutical composition for treatment of breast cancer comprising: a compound
wherein the compound is selected from:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;
N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-(5-((m-tolylamino)methyl)-1H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide; and
a pharmaceutically acceptable salt thereof;
and one or more pharmaceutically acceptable excipients.

4. The pharmaceutical composition as claimed in claim 3, wherein the composition is for oral administration and comprises at least one of a tablet, a capsule, a granule, a powder, a liquid, a suspension, a syrup, an emulsion, and an elixir.

5. The pharmaceutical composition as claimed in claim 3, wherein the composition is for parental administration and comprises at least one of an emulsion, a suspension, a sterile solution, an injectable, and a powder for constituents.

6. The pharmaceutical composition as claimed in claim 3, wherein the composition is for transdermal administration and comprises at least one of a cream, an ointment, a gel, a foam, a spray, a solution, an emulsion, a suspension, and a transdermal patch.

7. A method of treating breast cancer comprising administering to a patient a pharmaceutically effective amount of at least one of a compound or its pharmaceutically acceptable salts and a pharmaceutical composition comprising an effective amount of the compound or its pharmaceutically acceptable salts,
wherein the compound is selected from the group consisting of:
N-(5-chloro-2-methoxyphenyl)-2-((5-((m-tolylamino)methyl)-1H-1,2,4-triazol-3-yl)thio)acetamide;
N-Phenyl-2-((5-((m-tolylamino)methyl)-1H-1,2,4-triazol-3-yl)thio)acetamide;
N-(3-fluorophenyl)-2-((5-((m-tolylamino)methyl)-1H-1,2,4-triazol-3-yl)thio)acetamide;
N-(3-bromophenyl)-2-((5-((m-tolylamino)methyl)-1H-1,2,4-triazol-3-yl)thio)acetamide;
N-(4-methoxyphenyl)-2-((5-((m-tolylamino)methyl)-1H-1,2,4-triazol-3-yl)thio)acetamide;
N-(3,4-dichlorophenyl)-2-((5-((m-tolylamino)methyl)-1H-1,2,4-triazol-3-yl)thio)acetamide;
N-(3,5-dimethoxyphenyl)-2-((5-((m-tolylamino)methyl)-1H-1,2,4-triazol-3-yl)thio)acetamide;
N-(2-chloro-5-(trifluoromethyl)phenyl)-2-(5-((m-tolylamino)methyl)-1H-1,2,4-triazol-3-yl)thio)acetamide;
N-phenyl-2-((5-((phenylamino)methyl)-1H-1,2,4-triazol-3-yl)thio)acetamide;
N-(3-fluorophenyl)-2-((5-((phenylamino)methyl)-1H-1,2,4-triazol-3-yl)thio)acetamide;
N-(3-bromophenyl)-2-((5-((phenylamino)methyl)-1H-1,2,4-triazol-3-yl)thio)acetamide;
N-(4-methoxyphenyl)-2-((5-((phenylamino)methyl)-1H-1,2,4-triazol-3-yl)thio)acetamide;
N-(3,4-dichlorophenyl)-2-((5-((phenylamino)methyl)-1H-1,2,4-triazol-3-yl)thio)acetamide;
N-(3,5-dimethoxyphenyl)-2-((5-((phenylamino)methyl)-1H-1,2,4-triazol-3-yl)thio)acetamide;
N-(2-chloro-5-(trifluoromethyl)phenyl)-2-((5-((phenylamino)methyl)-1H-1,2,4-triazol-3-yl)thio)acetamide;
N-(5-chloro-2-methoxyphenyl)-2-((5-((phenylamino)methyl)-1H-1,2,4-triazol-3-yl)thio)acetamide; and
a pharmaceutically acceptable salt thereof;
wherein the administering is through at least one of an oral, parental, and transdermal route.

* * * * *